US00PP26734P3

(12) United States Plant Patent
Cook

(10) Patent No.: US PP26,734 P3
(45) Date of Patent: May 17, 2016

(54) *GARDENIA JASMINOIDES* PLANT NAMED 'GENIE-2'

(50) Latin Name: *Gardenia jasminoides*
Varietal Denomination: Genie-2

(71) Applicant: Allyn Cook, Gainesville, FL (US)

(72) Inventor: Allyn Cook, Gainesville, FL (US)

( * ) Notice: Subject to any disclaimer, the term of this patent is extended or adjusted under 35 U.S.C. 154(b) by 14 days.

(21) Appl. No.: 13/999,182

(22) Filed: Jan. 27, 2014

(65) Prior Publication Data

US 2015/0216096 P1 Jul. 30, 2015

(51) Int. Cl.
*A01H 5/02* (2006.01)

(52) U.S. Cl.
USPC ..... Plt./255

(58) Field of Classification Search
USPC ..... Plt./255
See application file for complete search history.

(56) References Cited

U.S. PATENT DOCUMENTS

PP21,983 P2 * 6/2011 Lee ..... Plt./255

* cited by examiner

*Primary Examiner* — Anne Grunberg

(57) ABSTRACT

A new and distinct variety of *Gardenia jasminoides* plant named 'Genie-2', characterized by its dense, low-profile growth habit, dark green foliage color and abundant fragrant, triple-whorl white flowers is disclosed.

3 Drawing Sheets

Genus and species: *Gardenia jasminoides.*
Varietal denomination: 'Genie-2'.

FIELD OF INVENTION

The present invention relates to a new and distinct variety of the genus *Gardenia* and a member of the Rubiaceae family. This new *Gardenia* variety, hereinafter referred to as 'Genie-2', was discovered by Allyn Austin Cook in June. 2007. 'Genie-2' is characterized by its dense, low-profile growth habit, dark green foliage color and abundant fragrant, triple-whorl white flowers.

BACKGROUND OF THE INVENTION

'Genie-2' is derived and selected from gifted, unnamed, without traceable lineage and unpatented seed planted in Alachua County, Fla. Seed was received en masse in 2005. Ten (10) of the seeds were planted. After two (2) years, only one (1) grew with distinction. The exceptional plant subsequently named 'Genie-2' grew with a low and mounded profile and was a prolific bloomer.

The value of this new cultivar lies in its low-profile growth habit, compact dark green foliage color and abundant fragrant triple-whorl white flowers. The remarkable attributes of 'Genie-2' are its small size, low-profile growth habit, heat tolerance and disease resistance. 'Genie-2' is well suited for use in either formal or informal groupings and is quite attractive in mass plantings. 'Genie-2' is appropriate, adaptable and quite attractive as a container plant. 'Genie-2' is responsive to pruning and training and may be maintained without an excessive amount of care. Its natural propensity to remain small to maturity makes it valuable for landscape uses in any garden size.

Asexual propagation of the new plant by cuttings has been under Dr. Cook's direction and control in Alachua and Hillsborough counties of Florida. The new plant retains its distinctive characteristics and reproduces true to type in successive generations of asexual reproduction.

SUMMARY OF THE INVENTION

The following are the most outstanding and distinguishing characteristics of this new cultivar when grown under normal horticultural practices in Alachua County, Fla. The combination of these characteristics distinguishes 'Genie-2' from all other varieties in commerce known to the inventor. 1. Dense and low-profile in nature. 2. Attractive dark green foliage. 3. The flowers are triple whorl, white, fragrant and profuse. 4. Reaches mature size under normal fertilization and moisture conditions. 5. Hardy to Zone 7. 6. Tolerates part sun to part shade. 7. Heat tolerant. 8. Adaptable to a wide range of soil types. 9. Easily propagated with semi-hardwood cuttings in late spring through summer or through the process known in the industry as "tissue culture." 10. Requires little pruning but is tolerant if pruning is desired. 11. Relatively pest resistant. 12. Very desirable in containers.

DESCRIPTION OF THE DRAWINGS

This new *Gardenia jasminoides* cultivar is illustrated by the accompanying photographic prints. The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Descriptions of colors in ordinary terms are presented where appropriate for clarity in meaning.

BOTANICAL DESCRIPTION OF THE PLANT

Figure 1:
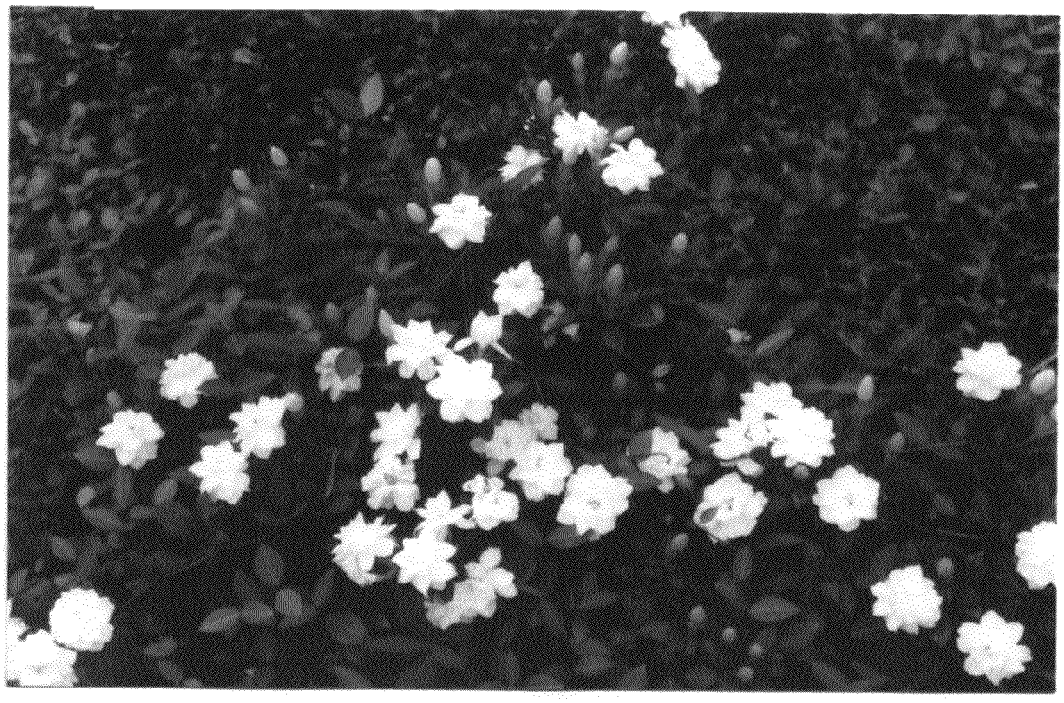
FIG. 1 shows the overall appearance of a plant of 'Genie-2' planted in the ground.
Figure 2:
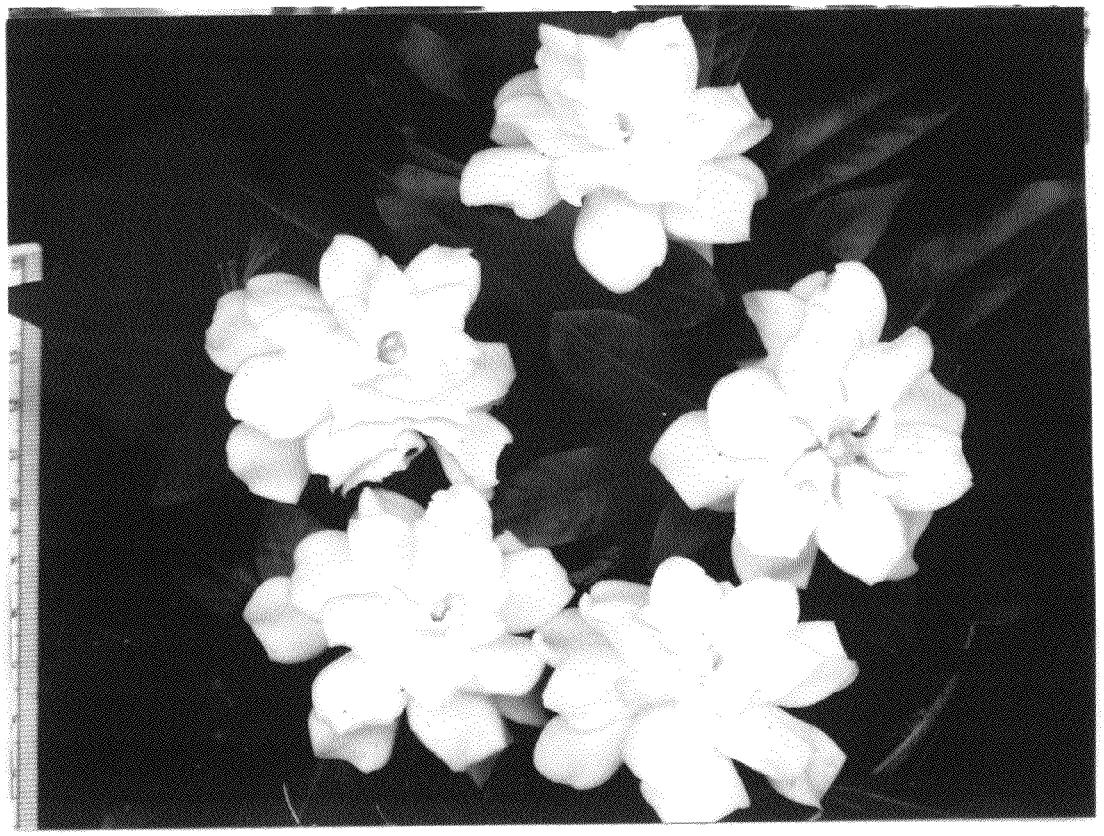
FIG. 2 shows a close-up view of a flower of 'Genie-2'.
Figure 3:
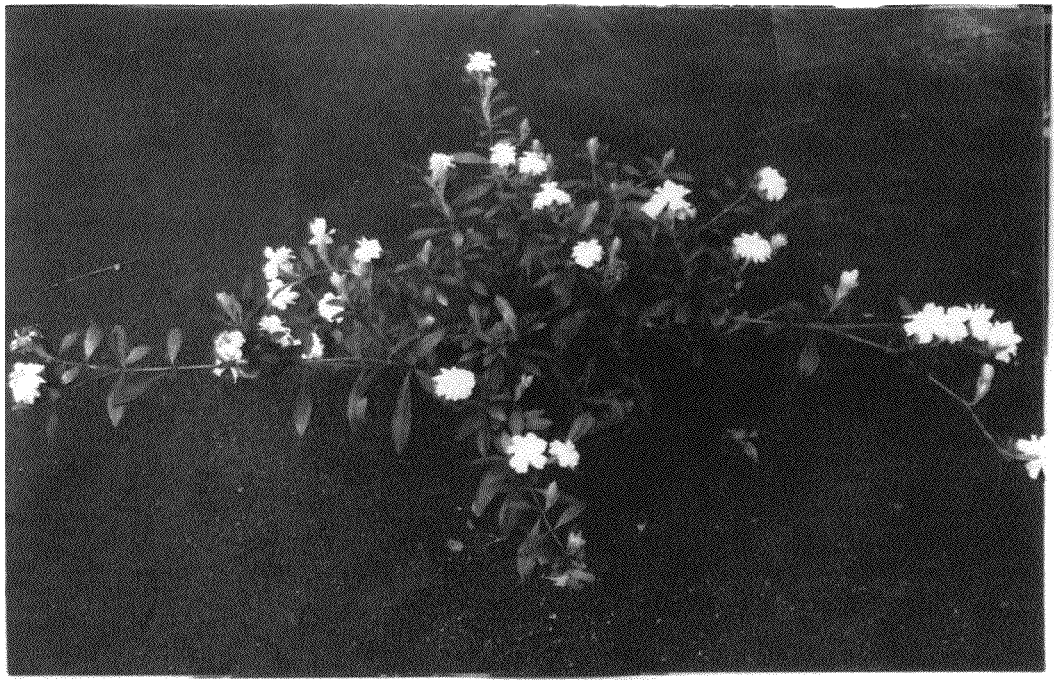
FIG. 3 shows the overall appearance of a plant of 'Genie-2' in a container.

The following is a detailed description of the new variety of *Gardenia* based on observations made of two-year-old plants grown in one to three gallon containers and in established landscape plantings in Alachua and Hillsborough Counties, Fla., utilizing common gardening techniques. The description includes a comparison with *Gardenia jasminoides* 'Leeone' (U.S. Plant Pat. No. 21,983) and *Gardenia jasminoides* 'Daisy' (unpatented).

TABLE 1

COMPARATIVE CHARACTERISTICS

| Genus species | *Gardenia jasminoides* | *Gardenia jasminoides* | *Gardenia jasminoides* |
|---|---|---|---|
| Varietal denomination | 'Genie-2' | 'Leeone' | 'Daisy' |
| Height (Mature) | 1-1½' (0.3-0.5 m) | 3-4' (0.9-1.2 m) | 3-3½' (0.9-1.05 m) |
| Width (Mature) | 2-3' (0.6-0.9 m) | 2½-3' (0.75-0.9 m) | 3-3½' (0.9-1.05 m) |
| Leaf Length | 1⅝-2⅜" (4.1-6.0 cm) | 1½-2¾" (3.8-7 cm) | 1¼-2¼" (3.1-5.7 cm) |
| Leaf Width | ¼-¾" (0.7-2.0 cm) | ⅝-1⅛" (1.6-2.9 cm) | ⅝-1 3/16" (1.6-3.02 cm) |
| Leaf Shape | Elliptic-Lanceolate | Elliptic-lanceolate | Ovate-rounded |
| Growth Habit | Dense, Low-profile | Dense upright | Dense globose |
| Flower Form | Triple | Double | Single |
| Bloom Period | May-August | May-November | May-October |

*Gardenia jasminoides* 'Leeone' and *Gardenia jasminoides* 'Daisy' are well known in the industry and are comparable to 'Genie-2' in that all have green foliage color and white fragrant blooms. However, there are many differences. The growth habit of 'Genie-2' is compact, dense and low in profile to a mature height of 1½' (0.5 m) tall compared to 'Leeone' which is upright, globose and much taller—4' (1.2 m) tall. The flower form of 'Genie-2 is a triple whorl where 'Leeone' is double and 'Daisy' is single.

DETAILED DESCRIPTION

In the following description, color references are made to The Royal Horticultural Society Colour Chart, 2001 Edition, except where general terms of ordinary dictionary significance are used. Plants used for the description were approximately 2 years old and were grown in 1-3 gallon containers in part shade outdoor conditions in Alachua County, Fla.

Botanical classification: 'Genie-2' is a cultivar of '*Gardenia jasminoides*'.

Parentage: "Genie-2' is derived and selected from seed received as a gift, unnamed and without traceable lineage planted in Alachua County, Fla. Seed was received en masse in 2005.

Plant description: The claimed variety is a compact, low-profile evergreen shrub. The plant is hardy in USDA Zones 7 to 9.

*Propagation*.—Stem cuttings. Time to initiate roots in summer: approximately 4 weeks. Tissue culture.

*Root description*.—Numerous, fibrous and well-branched.

*Plant size*.—About 30 cm high from the soil level to the top of the foliage and about 60 cm wide after 2 years.

*First year stems*.—Diameter of 3-5 mm. Shape: round. Color: 137A.

*Stem strength*.—Flexible when young, more easily broken once mature.

*Internode length*.—Partially dependent upon sun exposure; 1.5-2 cm.

*Second year and older stems*.—Diameter of 5-8 mm or more. Shape: round. Color: N199B.

Foliage description:

*Arrangement*.—Opposite. Mature foliage color: 147A upper Surface, 146B undersurface.

*Shape*.—Elliptical. Apex: acuminate. Base: cuneate. Margin: entire to revolute.

*Texture*.—Glabrous, lustrous.

*Venation*.—Pinnate. Petiole length: 1-2 mm.

Flower description:

*Flower type and habit*.—Flowers are borne singly from mid branch to the distal end. Individual flowers are showy for about 4 days and remain on the plant for 1 to 2 weeks after they have senesced. Bloom period: Spring, Flowers are produced abundantly from May to June and then sporadically through August in Alachua County, Fla. Fragrance: Exceedingly sweet fragrance.

*Flower diameter*.—About 5 cm. Height or depth: About 3.5 cm.

*Flower bud diameter*.—About 1 cm. Flower bud length: about 2.5 cm. Flower bud shape: oblong. Color: 144A.

Petals:

*Quantity*.—6 to 8 true petals and 16 to 18 petaloids per flower.

*True petal length*.—About 1 cm. Width: About 0.9 cm. Shape: obovate with entire, undulating margins and overlapping in arrangement to form a whorl. Texture: Thick, glabrous.

*Petaloid petal length*.—0.3 to 0.5 cm, becoming smaller toward the center of the flower. Shape: Obovate. Texture: Thick, glabrous. Color: At peak bloom the upper and lower surfaces 155C.

Stamens; pistils: There is no physical evidence of reproductive structures despite the common appearance of the colored imprints.

Fruit: None observed.

Disease/pest resistance: No specific pest or disease resistance or susceptibility has been observed, however the variety performs well under normal disease pressures in Alachua County, Fla.

What is claimed is:

1. A new and distinct variety of *Gardenia jasminoides* plant named 'Genie-2', substantially as illustrated and described herein.

* * * * *